United States Patent
Putnam et al.

(10) Patent No.: US 11,376,276 B2
(45) Date of Patent: Jul. 5, 2022

(54) LUBRICATING BLOCK COPOLYMERS AND THEIR USE AS BIOMIMETIC BOUNDARY LUBRICANTS

(71) Applicant: CORNELL UNIVERSITY, Ithaca, NY (US)

(72) Inventors: David Putnam, Ithaca, NY (US); Lawrence Bonassar, Ithaca, NY (US); Zhexun Sun, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 239 days.

(21) Appl. No.: 16/339,474

(22) PCT Filed: Oct. 4, 2017

(86) PCT No.: PCT/US2017/055057
§ 371 (c)(1),
(2) Date: Apr. 4, 2019

(87) PCT Pub. No.: WO2018/067648
PCT Pub. Date: Apr. 12, 2018

(65) Prior Publication Data
US 2019/0231811 A1 Aug. 1, 2019

Related U.S. Application Data

(60) Provisional application No. 62/403,962, filed on Oct. 4, 2016.

(51) Int. Cl.
*A61K 31/785* (2006.01)
*A61K 31/795* (2006.01)
*C08F 293/00* (2006.01)
*A61P 19/02* (2006.01)
*C08F 120/06* (2006.01)
*C08F 220/28* (2006.01)

(52) U.S. Cl.
CPC .......... *A61K 31/785* (2013.01); *A61K 31/795* (2013.01); *C08F 220/286* (2020.02); *C08F 293/005* (2013.01); *C08F 2438/03* (2013.01)

(58) Field of Classification Search
CPC ... A61K 31/785; A61K 31/795; C08F 220/34; C08F 293/005; C08F 2438/03
See application file for complete search history.

(56) References Cited

U.S. PATENT DOCUMENTS

| 6,024,954 A | * | 2/2000 | Park et al. |
| 10,344,243 B2 | | 7/2019 | Putnam et al. |
| 2009/0018270 A1 | * | 1/2009 | Crooks et al. |

FOREIGN PATENT DOCUMENTS

| CN | 104870020 A | 8/2015 |
| CN | 105073155 A | 11/2015 |
| JP | 2010-134419 A | 6/2010 |
| WO | 02/077075 A1 | 10/2002 |
| WO | 2014/063102 A1 | 4/2014 |
| WO | 2015/054452 A1 * | 4/2015 |
| WO | 2016/014408 A1 | 1/2016 |

OTHER PUBLICATIONS

Wang et al. (Journal of Applied Polymer Science, Published Jan. 9, 2016, pp. 1-8) (Year: 2016).*
O'Reilly (Polymer Chemistry, Published 2010, pp. 149-157) (Year: 2010).*
Jacquin, M. et al., "Characterization of Amphiphilic Diblock Copolymers Synthesized by MADIX Polymerization Process", Macromolecules, vol. 40, pp. 2672-2682 (2007).
Extended Supplementary European Search Report dated May 8, 2020 in European Patent Application No. 17 85 9078.2.
Hernandez-Barajas J. et al., "Inverse-emulsion copolymerization of acrylamide and quaternary ammonium cationic monomers with block copolymeric surfactants: copolymer composition control using batch and semi-batch techniques", Polymer, (1997), vol. 38, No. 2, pp. 449-458.
Loiseau J. et al., "Synthesis and Characterization of Poly(acrylic acid) Produced by RAFT Polymerization. Application as a Very Efficient Dispersant of CaCO3, Kaolin, and TiO2", Macromolecules, (2003), 36, pp. 3066-3077.
Notice of Reason(s) for Rejection dated Oct. 5, 2021 received in Japanese Patent Application No. 2019-518233.

* cited by examiner

*Primary Examiner* — Alma Pipic
(74) *Attorney, Agent, or Firm* — Scully, Scott, Murphy & Presser, P.C.

(57) ABSTRACT

The invention relates to methods of lubricating biological tissue, such as joints, bone, ocular tissue, nasal tissue, tendons, tendon capsule, and vaginal tissue, by contacting the biological tissue with an effective amount of a block copolymer lubricating composition which functions at least or better than lubricin. In particular embodiments, the method is used to treat osteoarthritis. In specific embodiments, the block copolymer has an ammonium-containing polymer block and a non-ionic hydrophilic polymer block, or the copolymer has a carboxylic acid-containing polymer block and a non-acid non-ionic hydrophilic polymer block.

12 Claims, 6 Drawing Sheets

Specification includes a Sequence Listing.

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: synthetic peptides

<400> SEQUENCE: 1

Thr Lys Lys Thr Leu Arg Thr
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptides

<400> SEQUENCE: 2

Ser Gln Asn Pro Val Gln Pro
1               5

<210> SEQ ID NO 3
<211> LENGTH: 6
```

```
<212> TYPE: PRT
<213> ORGANISM: Artificial Sequence
<220> FEATURE:
<223> OTHER INFORMATION: synthetic peptides

<400> SEQUENCE: 3

Trp Tyr Arg Gly Arg Leu
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptides

<400> SEQUENCE: 4

Ser Tyr Ile Arg Ile Ala Asp Thr Asn
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptides

<400> SEQUENCE: 5

Cys Gln Asp Ser Glu Thr Arg Phe Tyr
1               5
```

LUBRICATING BLOCK COPOLYMERS AND THEIR USE AS BIOMIMETIC BOUNDARY LUBRICANTS

CROSS-REFERENCE TO RELATED APPLICATIONS

This application claims priority under 35 U.S.C. § 119(e) to provisional application U.S. Ser. No. 62/403,962, filed Oct. 4, 2016, which is incorporated herein in its entirety.

STATEMENT REGARDING FEDERALLY SPONSORED RESEARCH

This invention was made with government support under Grant No. AR066667-01 awarded by the National Institutes of Health. The government has certain rights in the invention.

INCORPORATION BY REFERENCE OF SEQUENCE LISTING

The Sequence Listing in the ASCII text file, named as 34159_7566_03_US_SequenceListing.txt of 2 KB, created on Feb. 17, 2022, and submitted to the United States Patent and Trademark Office via EFS-Web, is incorporated herein by reference.

FIELD OF THE INVENTION

This invention generally relates to pharmaceutically acceptable lubricating compositions and their use in methods of lubricating biological tissue, especially joint, cartilage, and bone surfaces. The invention more particularly relates to polymeric compositions that mimic the action of lubricin, and more particularly, to methods of using such compositions for treating a variety of conditions, such as osteoarthritis, where lubrication is especially beneficial in treating and ameliorating the effects of the disease or condition.

BACKGROUND OF THE INVENTION

Lubricin is a glycosylated protein found in synovial fluid, plays a pivotal role in joint boundary lubrication and prevention of osteoarthritis. Lubricin reduces the coefficient of friction (COF) of articular cartilage in the boundary mode by as much as 70 percent (Gleghorn, J. P. et al., *J. Orthop. Res.* 2009, 27 (6), 77). This potent lubricating ability arises from the structure of lubricin: a central mucin-like domain of lubricin consists of an extensively glycosylated core protein that attracts and retains water near the molecule; and the C-terminus of lubricin binds the protein to the cartilage surface (Zappone, B. et al., *Langmuir* 2008, 24 (4), 1495). This architecture is crucial to the boundary mode lubrication of articular cartilage as denaturation in either domain of lubricin would cause partial or complete loss of lubrication capacities.

Osteoarthritis (OA) afflicts over 50 million individuals in the developed world and this number is expected to rise as median age and life expectancy increase. The economic impact of osteoarthritis treatment exceeds $30 billion annually in the United States alone. The financial burden, as well as other factors (i.e., quality of life, loss of labor hours, etc.) incentivizes development of more effective treatments.

Current treatments for osteoarthritis include non-steroidal anti-inflammatories, intra-articular corticosteroid injections, and chondroitin sulfate or glucosamine supplements. However, all of these treatments have little or no effect on disease progression. A more recent approach to the treatment of OA is the intra-articular injection of the natural synovial fluid glycosaminoglycan, hyaluronic acid (HA) (e.g., Mabuchi et al. (1994) *J. Biomed. Mat. Res.* 28:865-70), where HA is known to increase synovial fluid viscosity (e.g., viscosupplementation) to reduce the coefficient of friction in the hydrodynamic mode of lubrication (e.g., Tadmor et al. (2002) *J. Biomed. Mat. Res.* 61:514-23). The other predominant lubrication component in synovial fluid is lubricin, a high molecular weight glycoprotein that reduces the coefficient of friction in the boundary mode of lubrication.

In damaged cartilage, it is well known that chondrocyte production of lubricin is compromised and boundary mode lubrication is reduced. Natural lubricants, such as proteoglycan aggregates and mucins (e.g., lubricin), keep natural surfaces hydrophilic. Intra-articular injection of supplemental lubricin, as well as the truncated recombinant lubricin construct LUB:1, have been shown to slow progression of OA in rat models of disease (e.g., Jay et al. (2010) *Arthritis Rheum.* 62:2382-91; Flannery et al. (2009) *Arthritis Rheum.* 60:840-7). However, to date, the large-scale recombinant manufacture of both lubricin and LUB:1 remains challenging owing to multiple amino acid repeats in the protein core, as well as the high degree of glycosylation (e.g., Jay (2004) *Curr. Opin. Orthop.* 15:355-359; Jones et al. (2007) *J. Orthop. Res.* 25:283-292). There is also a separate need for an effective lubricating agent for bone in situations where direct bone-on-bone contact occurs, as may occur in the advanced stages of osteoarthritis. Consequently, effective lubricating agents that could provide the same or similar boundary lubrication as lubricin or LUB:1 would be a significant advance in the field.

SUMMARY OF THE INVENTION

The present disclosure is directed to the design, synthesis, and use of specialized block copolymers having a lubricin-mimetic structure and which provide substantial lubrication capacity under boundary mode lubrication conditions. In particular embodiments, the block copolymer contains a lubrication block (e.g., $M_n \sim 200$ kDa) that mimicks the mucin-like domain of lubricin and a smaller cartilage-binding block (e.g., $M_n \sim 3$ kDa) that mimicks the hemopexin-like domain. As disclosed later on in this application, applying this type of polymer to lubricin-deficient bovine articular cartilage or bone resulted in a significantly reduced coefficient of friction (COF) compared to untreated controls.

In one aspect, the invention is directed to block copolymers having the following structure:

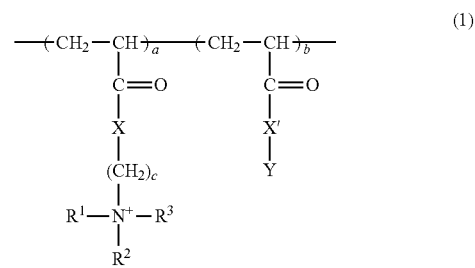

(1)

wherein: $R^1$, $R^2$, and $R^3$ are independently selected from hydrocarbon groups having at least one and up to twelve carbon atoms; X and X' are independently selected from —NR'—, —O—, and a bond, wherein R' is selected from hydrogen atom and hydrocarbon groups having at least one and up to six carbon atoms; Y is selected from polyalkylene glycol, saccharide, and polyalcohol; subscripts a and b are independently integers of at least 3; and subscript c is an integer of at least 1. In accordance with the laws of chemistry, the block copolymer is terminated on each end by terminal groups, and the total positive charge of quaternary ammonium groups in the copolymer is counterbalanced by a total negative charge of equivalent magnitude provided by anions associated with the ammonium groups.

In another aspect, the invention is directed to block copolymers having the following structure:

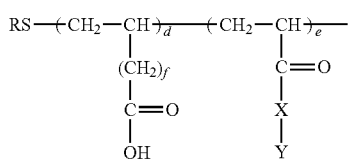
(2)

wherein: X is selected from —NR'—, —O—, and a bond, wherein R' is selected from hydrogen atom and hydrocarbon groups having at least one and up to six carbon atoms; Y is selected from polyalkylene glycol, saccharide, and polyalcohol; R is a hydrogen atom, hydrocarbon group (R) having 1-12 carbon atoms, or a cartilage binding domain; subscripts d and e are independently integers of at least 3; and subscript f is 0 or an integer of at least 1. In the formula, the hydrogen atom on the shown carboxylic acid group is optionally replaced with a positively charged metal ion or positively charged organic group. In accordance with the laws of chemistry, the block copolymer is terminated on the end opposite to the thiol group by a terminal group.

In another aspect, the instant invention relates to methods for imparting a suitable level of lubricity to a biological tissue by contacting the biological tissue with a sufficient amount of a lubricating composition to increase the lubricity of the biological tissue. The lubricating composition can be, for example, any of the block copolymers described above. The biological tissue can be selected from, for example, joints, bone, ocular tissue, nasal tissue, tendons, tendon capsule, and vaginal tissue.

BRIEF DESCRIPTION OF THE FIGURES

FIG. 5A is a graph plotting COF as a function of concentration of the diblock copolymer of FIG. 1. FIG. 5B is a graph plotting COF as a function of incubation time, with 1 mg/mL of copolymer for different durations. The resulting graph can be considered a binding kinetics curve.

FIGS. 6A and 6B are graphs plotting the COF of trabecular and subchondral bone samples, respectively, treated with the diblock copolymer (3) solution (10 mg/mL for 2 hours or 1 mg/mL for 1 hour) or PBS solution.

DETAILED DESCRIPTION OF THE INVENTION

Figure 1:
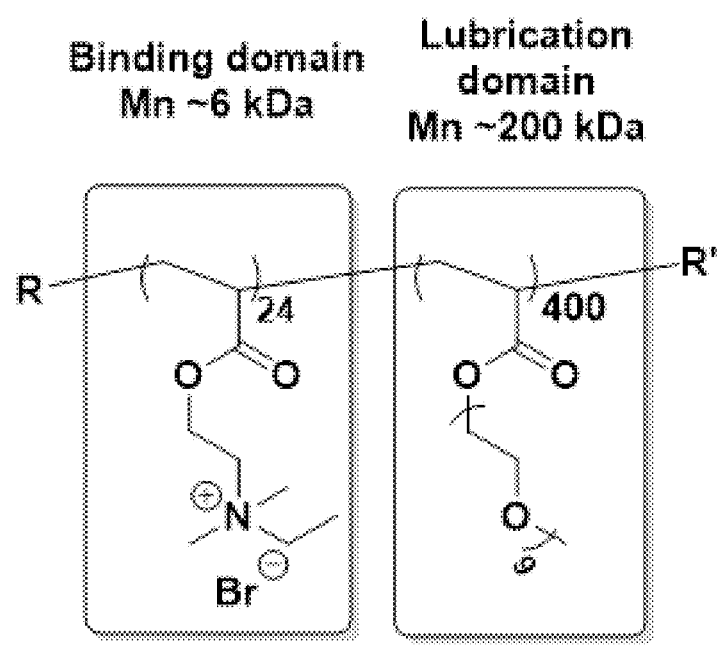
FIG. 1. General representation of an exemplary diblock copolymer of the invention, with binding block and lubricating block portions identified.

In a first aspect, the invention is directed to block copolymers that mimic lubricin by having a mucin-like domain and a C-terminal hemopexin-like (PEX-like) domain. The copolymer may, for example, contain a polymer block containing positively or negatively charged pendant groups and a polymer block containing pendant non-ionic hydrophilic groups, particularly hydrophilic groups containing ether and/or hydroxy functional groups. In the case where the pendant group is polymeric, the copolymer can be further classified as a graft brush copolymer. The term "copolymer," as used herein, refers to the presence of at least two polymer blocks. The copolymer may be, for example, a diblock copolymer, triblock copolymer, tetrablock copolymer, or higher copolymer.

A first class of block copolymers considered herein is encompassed by the following generic structure:

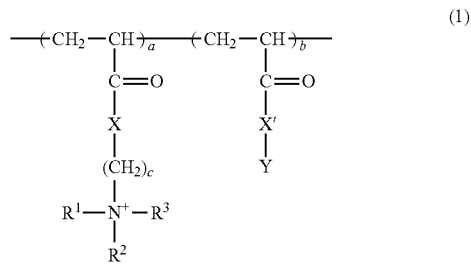
(1)

The substituents $R^1$, $R^2$, and $R^3$ in Formula (1) are independently selected from hydrocarbon groups (R) having at least one and up to twelve carbon atoms. The substituents $R^1$, $R^2$, and $R^3$ may, in some embodiments, be more particularly defined as having precisely one, two, three, four, five, six, seven, eight, nine, ten, eleven, or twelve carbon atoms, or a particular range of carbon atoms therein, e.g., 1-10, 1-8, 1-6, 1-4, 1-3, 2-12, 2-10, 2-8, 2-6, 2-4, 3-12, 3-10, 3-8, or 3-6 carbon atoms. In some embodiments, $R^1$, $R^2$, and $R^3$ are all the same, while in other embodiments, $R^1$, $R^2$, and $R^3$ are not all the same (or at least two of $R^1$, $R^2$, and $R^3$ are different). The hydrocarbon group R can be saturated or unsaturated, straight-chained (linear) or branched, and cyclic or acyclic.

In one set of embodiments, at least one, two, or all of $R^1$, $R^2$, and $R^3$ are selected from hydrocarbon groups composed solely of carbon and hydrogen. The hydrocarbon group composed solely of carbon and hydrogen can be, for example, an alkyl, alkenyl, cycloalkyl, cycloalkenyl (aliphatic), or aromatic group. Some examples of straight-chained alkyl groups include methyl, ethyl, n-propyl, n-butyl, n-pentyl, n-hexyl, n-heptyl, n-octyl, n-nonyl, n-decyl, n-undecyl, and n-dodecyl groups. Some examples of branched alkyl groups include isopropyl (2-propyl), isobutyl (2-methylprop-1-yl), sec-butyl (2-butyl), t-butyl, 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, and isohexyl (4-methylpent-1-yl), wherein the "1-yl" suffix represents the point of attachment of the group. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, and 4-penten-1-yl groups. Some examples of branched olefinic groups include propen-2-yl, 3-buten-2-yl ($CH_2$=CH—CH.—$CH_3$), 3-buten-3-yl ($CH_2$=C.—$CH_2$—$CH_3$), 4-penten-2-yl, 4-penten-3-yl, 3-penten-2-yl, 3-penten-3-yl, and 2,4-pentadien-3-yl, wherein the dot in the foregoing exemplary formulas represents a radical (i.e., the point of attachment of the group). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkenyl (aliphatic) groups include cyclopropenyl, cyclobutenyl, cyclopentenyl, cyclopentadienyl, cyclohexenyl, cyclohexadienyl, cycloheptenyl, cycloheptadienyl, cyclooctenyl, cyclooctadienyl, and cyclooctatetraenyl groups. Some examples of aromatic groups include phenyl and benzyl. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene.

In another set of embodiments, at least one of $R^1$, $R^2$, and $R^3$ is selected from hydrocarbon groups containing at least one heteroatom (i.e., non-carbon and non-hydrogen atom), such as one or more heteroatoms selected from oxygen, nitrogen, sulfur, and halide atoms, as well as groups containing one or more of these heteroatoms (i.e., heteroatom-containing groups). In some embodiments, the hydrocarbon group does not contain hydrogen atoms (e.g., where all hydrogen atoms are replaced with heteroatoms, such as in —$CF_3$), while in other embodiments, the hydrocarbon group contains at least one hydrogen atom. Some examples of oxygen-containing groups include hydroxy (OH), alkoxy (OR), carbonyl-containing (e.g., carboxylic acid, ketone, aldehyde, carboxylic ester, amide, and urea functionalities), nitro ($NO_2$), carbon-oxygen-carbon (ether), sulfonyl, and sulfinyl (i.e., sulfoxide) groups. Some particular examples of alkoxy groups (—OR) include methoxy, ethoxy, n-propoxy, isopropoxy, n-butoxy, isobutoxy, t-butoxy, phenoxy, benzyloxy, 2-hydroxyethoxy, 2-methoxyethoxy, 2-ethoxyethoxy, vinyloxy, and allyloxy groups. In the case of an ether group, the ether group can also be a polyalkyleneoxide (polyalkyleneglycol) group, such as a polyethyleneoxide group. Some examples of nitrogen-containing groups include primary amine, secondary amine, tertiary amine (i.e., —$NR'_2$ or $NR'^+_3$, wherein R' is independently selected from H and hydrocarbon groups set forth above), nitrile (CN), amide (i.e., —C(O)$NR'_2$ or —NRC(O)R', wherein R' is independently selected from hydrogen atom and hydrocarbon groups set forth above), imine (e.g., —CR'=NR', wherein R' is independently H or a hydrocarbon group), urea (—NR'—C(O)—$NR'_2$, wherein R' is independently H or a hydrocarbon group), and carbamate groups (—NR'—C(O)—OR', wherein R' is independently H or a hydrocarbon group). Some examples of sulfur-containing groups include mercapto (i.e., —SH), thioether (i.e., sulfide, e.g., —SR), disulfide (—R—S—S—R), sulfoxide (—S(O)R), sulfone (—$SO_2$R), sulfonate (—S(=O)$_2$OR", wherein R" is H, a hydrocarbon group, or a cationic group), and sulfate groups (—OS(=O)$_2$OR", wherein R" is H, a hydrocarbon group, or a cationic group). Some examples of halide atoms include fluorine, chlorine, bromine, and iodine. One or more of the heteroatoms described above (e.g., oxygen, nitrogen, and/or sulfur atoms) can be inserted between carbon atoms (e.g., as —O—, —NR'—, or —S—) in any of the hydrocarbon groups described above. Alternatively, or in addition, one or more of the heteroatom-containing groups can replace one or more hydrogen atoms on the hydrocarbon group. In some embodiments, any one or more of the above groups is excluded.

The variables X and X' in Formula (1) are independently selected from —NR'—, —O—, and a bond, wherein R' is selected from hydrogen atom and hydrocarbon groups (selected from R groups) having at least one and up to six carbon atoms. In some embodiments, R' is specifically selected from hydrogen atom, methyl, ethyl, n-propyl, isopropyl, n-butyl, sec-butyl, isobutyl, and t-butyl groups, or a more specific selection thereof.

In a first instance, the variable Y in Formula (1) is or includes a polyalkylene glycol group. The polyalkylene glycol group can be conveniently expressed by the following structure: (—CR'$_2$CR'$_2$O—)$_n$R', wherein R' is independently selected from hydrogen atom and hydrocarbon group (e.g., methyl or ethyl) for each instance of R', and n is at least 2, 3, 4, 5, or 6 and up to, for example, 8, 9, 10, 12, 15, 20, 25, 30, 35, 40, 50, 60, 70, 80, 90, 100, 200, 300, 400, or 500, or n is within a range bounded by any two of the foregoing values, wherein each of the foregoing values corresponds to the number of alkylene oxide (—CR'$_2$CR'$_2$O—) monomer units. In particular embodiments, the polyalkylene glycol is a polyethylene glycol or polypropylene glycol group. Moreover, the polyalkylene glycol group may or may not be integrated into a copolymer, such as a copolymer containing polyethylene glycol and an anionic polymer portion, such as polyacrylic acid (PAA), polyglutamic acid, or polyaspartic acid.

In a second instance, the variable Y in Formula (1) is or includes a saccharide group. The term "saccharide," as used herein, includes monosaccharides (contains one monosaccharide unit) and saccharides containing at least or more than two monosaccharide units, such as disaccharides, trisaccharides, oligosaccharides (e.g., at least 4 and up to 20, 30, 40, 50, or 60 monosaccharide units), and polysaccharides (generally greater than 60, 70, or 80 monosaccharide units, and up to, for example, 100, 200, 300, 400, 500, or 1000 monosaccharide units). The saccharide may also be derivatized in such a manner (e.g., esterified, etherified, aminated, or halogenated) that the derivatized version would still reasonably be classified as a saccharide by one skilled in the art. Some examples of monosaccharides include glucose, galactose, fructose, mannose, sialic acid, glucosamine, N-acetylglucosamine, and galacturonic acid. Some examples of disaccharides include lactose, sucrose, maltose, trehalose, cellobiose, and mannobiose. Some examples of oligosaccharides include the fructooligosaccharides (FOS), galactooligosaccharides (GOS), and mannanoligosaccharides (MOS). Some examples of polysaccharides include dextran, dextran sulfate, starch (e.g., amylose or amylopectin), cellulose, hemicellulose, polysialic acid, pectin, glycogen, mannan, galactomannan, xylan, pullulan, xanthan, carrageenan, guar gum, polygalacturonic acid, poly(N-acetylgalactosamine), heparin, hyaluronic acid, and chondroitin sulfate. In some embodiments, the saccharide is selected to have an overall anionic charge, such as in those saccharides having carboxylic acid, carboxylate, sulfate, or sulfonate groups. The saccharide group may or may not be integrated into a copolymer, such as a copolymer containing an oligosaccharide portion and an oligopeptide or polyacrylic acid portion. In some embodiments, the saccharide-containing copolymer contains a saccharide portion and an anionic polymer portion, such as polyacrylic acid (PAA), polyglutamic acid, or polyaspartic acid.

In a third instance, the variable Y in Formula (1) is or includes a polyalcohol group. The term "polyalcohol," as used herein, refers to non-saccharide groups having a multiplicity (i.e., at least 2, 3, or 4) of hydroxy groups. The polyalcohol may be, for example, a sugar alcohol or polyhydric alcohol. Some examples of sugar alcohols include erythritol, xylitol, mannitol, glycerol, and sorbitol. The saccharide or polyalcohol (as Y) is generally attached to the block copolymer of Formula (1) by one of its hydroxy groups in deprotonated form, wherein X' can represent the oxygen atom from the group Y; or X' can represent a bond, with Y representing a saccharide or polyalcohol bound by one its oxygen atoms to the shown C(O) group; or X' is —NR'—, with Y representing a saccharide or polyalcohol bound by one its carbon atoms to the —NR'— group. In other embodiments, the polyalcohol is a polymer that contains hydroxy groups. The hydroxy-containing polymer may include, for example, at least 2, 3, 4, 5, or 6 and up to, for example, 8, 9, 10, 12, 15, 20, 25, 30, 35, 40, 50, 60, 70, 80, 90, 100, 200, 300, 400, or 500 monomer units. Some examples of such polymers include polyvinylalcohol, poly(hydroxyethylmethacrylate), and poly(hydroxypropylmethacrylate). The polyalcohol group may or may not be integrated into a copolymer, such as a polyvinylalcohol-polyacrylic acid (PVA-PAA) copolymer. In some embodiments, the polyalcohol-containing copolymer contains a polyalcohol portion and an anionic portion, which may be an anionic polymer portion, such as polyacrylic acid (PAA), polyglutamic acid, or polyaspartic acid The subscripts a and b in Formula (1) are independently integers of at least 3, 4, 5, 6, 7, 8, 9, 10, 12, 15, 20, 25, 30, 35, 40, or 50. In some embodiments, subscripts a and b are independently no more than 30, 40, 50, 60, 70, 80, 90, 100, 150, 200, 250, 300, 350, 400, 450, 500, 600, 700, 800, 900, 1000, 1200, 1500, 1800, or 2000. In some embodiments, subscript a is selected to be smaller than subscript b. For example, subscript a may be within a range of 3-10, 3-20, 3-30, or 3-40 while subscript b is within a range of 30-500, 40-500, 50-500, or 60-500. In other embodiments, subscript a is selected to be larger than subscript b. For example, subscript a may be within a range of 30-500, 40-500, 50-500, or 60-500 while subscript b is within a range of 3-10, 3-20, 3-30, or 3-40.

Subscript c in Formula (1) is an integer of at least 1. In different embodiments, c is precisely 1, 2, 3, 4, 5, 6, 7, 8, 9, 10, 11, or 12, or c is within a range bounded by any two of the foregoing values. The value of c corresponds to the number of methylene groups subtended by c. That is, when subscript c is 1, a $CH_2$ linker is present between X and the quaternary ammonium group shown in Formula (1); and when subscript c is 2, a $CH_2CH_2$ linker is present between X and the quaternary ammonium group shown in Formula (1).

Although not shown in Formula (1), the structure depicted in Formula (1) necessarily (i.e., by the laws of chemistry) includes a terminating group on each of the two ends of the copolymer. The terminating group is independently selected from, for example, hydrogen atom, hydrocarbon groups R, or a heteroatom-containing group, such as —OH, —OCH$_3$, nitrile-containing alkyl (such as provided by the radical initiator or chain transfer agent), thiol (—SH), or dithioester group (as provided by a RAFT chain transfer agent). In some embodiments, at least one of the terminal groups is a thiol group. The terminating groups often correspond to groups originally present in precursor reactants used to synthesize the block copolymer, and thus, the type of terminating group is often dependent on the chemistry used to synthesize the block copolymer. Nevertheless, the terminating group may be suitably adjusted by reacting the initially produced block copolymer to append a specific terminating group, e.g., a cartilage binding domain (e.g., a peptide-containing group) which aids in binding the block copolymer to a desired biological tissue. In some embodiments, the cartilage binding domain is attached to the block copolymer via an —S— linker, as in the form RS—, where R is the cartilage binding domain. Moreover, although also not shown in Formula (1), the total positive charge of quaternary ammonium groups in the copolymer depicted in Formula (1) is counterbalanced by a total negative charge of equivalent magnitude provided by anions associated with the ammonium groups. The anions may be selected from any species acceptable for administration into a living organism, such as, for example, halides (e.g., chloride, bromide, or iodide), carbonate, bicarbonate, sulfate, bisulfate, bisulfite, carboxylates (e.g., acetate, propionate, butyrate, maleate, and citrate), mesylate), and sulfonates (e.g., mesylate).

A second class of block copolymers considered herein is encompassed by the following generic structure:

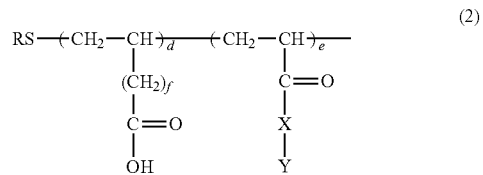

(2)

In Formula (2), the variables X and Y in Formula (2) are defined as provided above under Formula (1). The variable R is a hydrogen atom, hydrocarbon group (R) having 1-12 carbon atoms (or more particularly, at least 4, 5, or 6 and up to 7, 8, 9, 10, 11, or 12 carbon atoms), or a cartilage binding domain. Where R is a hydrocarbon group having 1-12 carbon atoms, the hydrocarbon group may be, more particularly, a linear or branched alkyl or alkenyl group. In some embodiments, the cartilage binding domain is a peptide-containing group (or "peptide"), which may be a monopeptide, dipeptide, tripeptide, or oligopeptide containing at least 4 and up to 5, 6, 7, 8, 9, or 10 peptide units. The cartilage-binding peptide may be, for example, TKKTLRT (SEQ ID NO: 1), SQNPVQP (SEQ ID NO: 2), WYRGRL (SEQ ID NO: 3), SYIRIADTN (SEQ ID NO: 4) or CQDSETRFY (SEQ ID NO: 5), a cholesterol or other sterol moiety, or any other moiety useful for binding the block copolymer to a biological tissue. Conjugation chemistry for attaching cartilage binding domains, hydrophobic alkyl chains, sterols, or other agents to the block copolymer are known to those of skill in the art. Although not shown, the structure in Formula (2) necessarily also includes a terminating group opposite to the RS—terminating group. The other terminating group can be as described above under Formula (1).

The subscripts d and e in Formula (2) are independently integers of at least 3, 4, 5, 6, 7, 8, 9, 10, 12, 15, 20, 25, 30, 35, 40, or 50. In some embodiments, subscripts d and e are independently no more than 30, 40, 50, 60, 70, 80, 90, 100, 150, 200, 250, 300, 350, 400, 450, 500, 600, 700, 800, 900, 1000, 1200, 1500, 1800, or 2000. In some embodiments, subscript d is selected to be smaller than subscript e. For example, subscript d may be within a range of 3-10, 3-20, 3-30, or 3-40 while subscript e is within a range of 30-500, 40-500, 50-500, or 60-500. In other embodiments, subscript d is selected to be larger than subscript e. For example, subscript d may be within a range of 30-500, 40-500, 50-500, or 60-500 while subscript e is within a range of 3-10, 3-20, 3-30, or 3-40.

Subscript f in Formula (2) is an integer of at least 1. In different embodiments, f is precisely 1, 2, 3, 4, 5, 6, 7, 8, 9, 10, 11, or 12, or f is within a range bounded by any two of the foregoing values. When subscript f is 1, a $CH_2$ linker is present. When subscript f is 2, a $CH_2CH_2$ linker is present.

In Formula (2), the hydrogen atom on the shown carboxylic acid group may be (i.e., is optionally) replaced with a positively charged metal ion or positively charged organic group. Some examples of positively charged metal ions include lithium, sodium, and potassium ions. Some examples of positively charged organic groups include ammonium ions, such as dimethyl, trimethyl, or tetramethyl ammonium ions.

The block copolymers described above may be synthesized by any suitable polymerization method. In particular embodiments, the block copolymers are synthesized by reversible addition-fragmentation chain-transfer (RAFT) polymerization, which is well known in the art. In the RAFT process, a first polymeric block is produced by reacting a first functionalized vinyl monomer (e.g., 2-(dimethylamino) ethyl acrylate, i.e., DMAEA) with a RAFT transfer agent (e.g., 4-cyanopentanoic acid dithiobenzoate, i.e., CPADB) in the presence of a polymerization initiator (e.g., 4,4'-Azobis (4-cyanopentanoic acid), i.e., ACPA). The first polymeric block is then reacted with a second functionalized vinyl monomer (e.g., poly(ethylene glycol) methyl ether acrylate) in the presence of a polymerization initiator to append a block of polymerized second functionalized vinyl monomer onto the first polymeric block.

The following scheme shows an exemplary RAFT process:

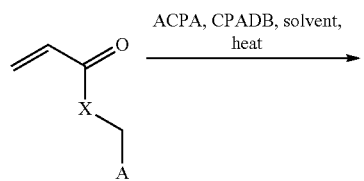

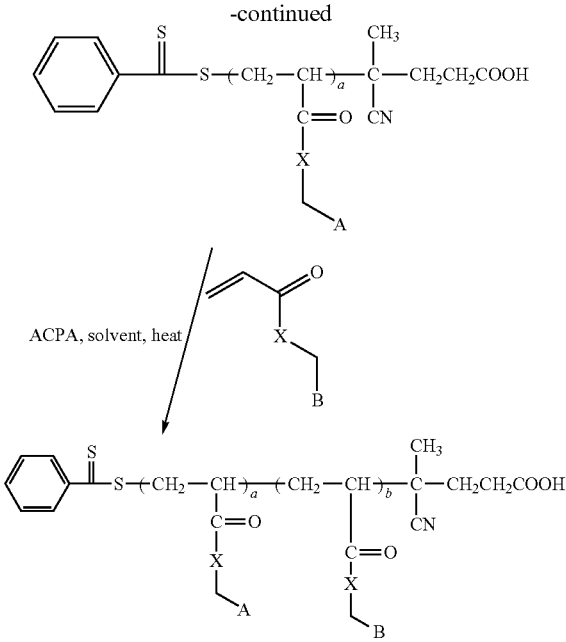

In another aspect, the invention is directed to a pharmaceutical formulation containing one or more block copolymers of the invention and a pharmaceutically-acceptable carrier (i.e., excipient or diluent). The pharmaceutical formulation can be prepared for use suitable for a variety of delivery forms, including for intraarticular, intranasal, intravaginal, or ocular delivery. The phrase "pharmaceutically acceptable carrier" or equivalent term, as used herein, refers to a pharmaceutically acceptable material, composition, or vehicle, which may be a liquid (diluent or excipient) or solid filler. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio. In the pharmaceutical composition, the compound is generally dispersed in the physiologically acceptable carrier, by either being mixed (e.g., in solid form with a solid carrier) or dissolved or emulsified in a liquid carrier. The carrier should be compatible with the other ingredients of the formulation and physiologically safe to the subject. Any of the carriers known in the art can be suitable herein depending on the mode of administration. Some examples of suitable carriers include aqueous solutions, gelatin, fatty acids (e.g., stearic acid) and salts thereof, talc, vegetable fats or oils, gums and glycols, starches, dextrans, and the like.

The pharmaceutical composition can also include one or more auxiliary agents, such as stabilizers, surfactants, salts, buffering agents, additives, or a combination thereof, all of which are well known in the pharmaceutical arts. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted by inclusion of a pH adjusting agent. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners, and the like may be necessary or desirable. The pharmaceutical formulation may be in the form of a sterile aqueous solution that contains one or more buffers, diluents, and/or other suitable additives such as, but not limited to, penetration enhancers and carrier compounds.

In another aspect, the invention is directed to methods for imparting lubricity to a biological tissue, such as to joints, cartilage, and bone, by using the biomimetic copolymers described above under Formulas (1) and (2). In the case of bone, the biomimetic copolymers can reduce the discomfort, pain, and additional damage resulting from direct bone-on-bone contact, as sometimes occurs in the advanced stages of osteoarthritis. In accordance with this method, biological tissue is contacted with a sufficient (i.e., effective or therapeutically-effective) amount of any of the copolymer compositions described above under Formulas (1) and (2) so as to increase the lubricity or to impart a suitable level of lubricity to the biological tissue. An increased level of lubricity generally corresponds to a lower level of friction (i.e., frictional coefficient, or coefficient of friction, COF) when the biological tissue slides against the same tissue or other material. Frictional coefficients can be measured using a tribometer, which evaluates surface lubrication by linear oscillation of a sample at variable speeds (generally, 0.1, 0.3, 1, 3, and 10 mm/s) and variable compressive normal stresses (generally 250 to 300 kPa).

As used herein, the terms "sufficient amount," "therapeutically-effective amount," and "effective amount" are used interchangeably to refer to an amount of a copolymeric composition of the invention that is sufficient to result in sufficient lubricity of a biological tissue, or the prevention of the development, recurrence, or onset of the disease or condition (e.g., osteoarthritis) or one or more symptoms thereof, or to enhance or improve the prophylactic effect(s) of another therapy, reduce the severity and duration of the disease or condition, ameliorate one or more symptoms of the disease or condition, prevent the advancement of disease or condition, and/or enhance or improve the therapeutic effect(s) of additional treatment(s).

A therapeutically-effective amount of the block copolymer can be administered to a patient in one or more doses sufficient to palliate, ameliorate, stabilize, reverse, or slow the progression of the disease or condition, or otherwise reduce the pathological consequences of the disease or condition, or reduce the symptoms of the disease or condition. The amelioration or reduction need not be permanent, but may be for a period of time ranging from at least one hour, at least one day, or at least one week, or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form, regimen, and the desired result. In certain embodiments of the invention, the therapeutically effective amount is an amount that is effective to treat osteoarthritis, achieves pain relief over a period of time, to improve joint movement and flexibility, to reduce friction in the joint or other accepted osteoarthritic measure of improvement. In exemplary embodiments, dosage levels range from about 0.1-10 mg/mL in injection volumes of 0.1-10 mL (for humans), and more typically about 1-5 mg/mL in an injection volume of 0.1 to 3 mL.

The biological tissue to be lubricated can be contacted with any of the block copolymers of Formulas (1) or (2) by any of the means well known in the medical arts. The biological tissue can be contacted with the block copolymer by, for example, injecting, infusing, implanting, spraying, or coating the block copolymer directly into or onto the biological tissue, or indirectly into biological tissue surrounding the tissue to be lubricated. In general, contacting a biological tissue means that the block copolymer is delivered to the tissue in any manner that leads to coating of the surface or bathing of the tissue with the copolymer. In certain embodiments, the tissue is contacted by injection or infusion of the composition into a joint space, thereby leading to a coating of cartilage and/or the meniscus found in that joint space. Moreover, the volumes used are at least partly dependent on the type of tissue being contacted, whether a space is being filled, or a surface is being coated, as could be determined by one skilled in the medical arts.

In particular embodiments, the block copolymer is injected or infused into or onto an arthritic or injured joint or bone to improve the lubricity of the joint or bone. As such, the copolymer provides boundary lubrication. The treatment may be specifically directed for treating or preventing osteoarthritis. The treatment of osteoarthritis or an injured joint, cartilage, or bone preferably results in reduction of symptoms, improved mobility, less joint pain, and overall inhibition of disease progression, or prophylaxis in the case of an injured joint. The method can also comprise administering one or more of the block copolymers described above along with simultaneous or sequential administration of another composition that functions to augment or work in tandem with the block copolymer while being outside the scope of Formulas (1) and (2). The augmenting (i.e., auxiliary) composition may be selected from, for example, hyaluronic acid, lubricin, synovial fluid, glycosaminoglycan, or other auxiliary agent. These other agents can also be administered by, for example, injection or infusion. In some embodiments, these other agents may work synergistically with one or more of the block copolymers described above to provide enhanced lubrication and wear protection.

In particular embodiments, the biological tissue is a joint, cartilage, or bone, and more typically, an injured or arthritic joint, cartilage, or bone. In some embodiments, the joint is a weight bearing joint, such as a hip, knee or ankle joint. Many different joints can benefit from an increased level of lubricity, including the shoulder, elbow, wrist, hand, finger and toe joints. Nevertheless, the biological tissue being lubricated is not limited to joints, cartilage, and bone. Other biological tissues that may be lubricated by use of the disclosed block copolymer include eye tissue, nasal tissue, and vaginal tissue. Thus, by use of the block copolymers described herein, a variety of conditions may be treated beyond those associated with joints, cartilage, and bone. Some of these other conditions include, for example, dry eye syndrome, dry nose, post-menopausal vaginal dryness, carpal tunnel syndrome, and more. Those skilled in the medical arts can determine the appropriate delivery route and method for contacting a particular biological tissue. For example, for dry eyes, contacting may be achieved by instilling drops; for dry nose, contacting may be achieved by nasal spray; for carpal tunnel syndrome contacting may be achieved by injecting near or around the inflamed tendon and capsule; and for post-menopausal dry vagina, a pill, troche or suppository can be placed in or implanted in the vagina. Hence, this method can be used to achieve boundary mode lubrication for any of a wide variety of biological tissues that could benefit from additional lubrication.

Examples have been set forth below for the purpose of illustration and to describe the best mode of the invention at the present time. However, the scope of this invention is not to be in any way limited by the examples set forth herein.

Examples

Synthesis and Characterization of a Lubricating Diblock Copolymer

In an effort to mimic lubricin's architecture, a diblock copolymer was herein prepared which included a large lubrication block ($M_n$~200 kDa) mimicking the mucin-like domain of lubricin and a small cartilage-binding block ($M_n$~3-10 kDa) mimicking the C-terminus domain. An exemplary composition showing the two mimicking domains is provided in FIG. 1. The lubrication domain of the diblock copolymer shown in FIG. 1 contains a polyacrylic acid backbone grafted with polyethylene glycol (PEG) brushes. The foregoing feature aids in hydration and resistance to compression in the polymer. The binding domain of the diblock copolymer shown in FIG. 1 contains a polyacrylic acid backbone having pendant quaternary ammonium groups that non-specifically interact with negatively-charged cartilage components, such as aggrecan. As further discussed below, applying this polymer to lubricin-deficient bovine articular cartilage resulted in a significantly reduced coefficient of friction (COF).

Synthesis of the diblock copolymer started with Reversible Addition-Fragmentation Chain-Transfer (RAFT) polymerization of 2-(dimethylamino)ethyl acrylate to synthesize the "pre-binding" block. A subsequent RAFT polymerization of poly(ethylene glycol) methyl ether acrylate ($M_n$ 480) added the lubrication block to the copolymer by using the "pre-binding" block as the macro-initiator. The tertiary amines in the "pre-binding" block were then converted into quaternary ammonium groups by treating the block copolymer with an excess of ethyl bromide to give the final product ($M_n$~200 kDa, PDI=1.8). A general schematic is provided as follows (with R and R' representing moieties provided by the RAFT chain transfer agent):

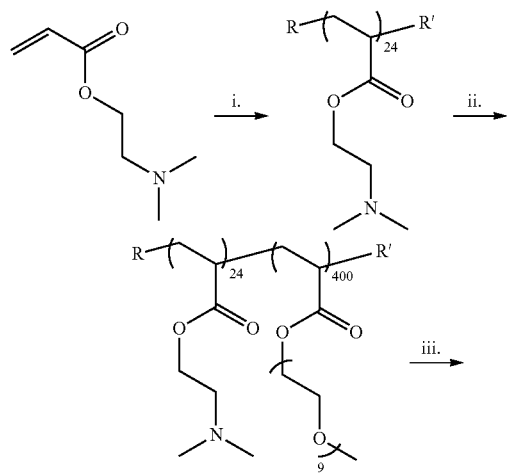

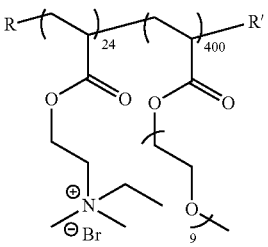

Synthesis of poly(2-(dimethylamino)ethyl acrylate) (1) with Degree of Polymerization (DP) of 24

2-(dimethylamino)ethyl acrylate (DMAEA) (4.30 g, 30 mmol) was added to a solution containing 14.0 mg (0.05 mmol) of 4,4'-azobis(4-cyanopentanoic acid) (ACPA), and 139.5 mg (0.5 mmol) of 4-cyanopentanoic acid dithiobenzoate (CPADB) in 5 mL of anisole. The mixture was deoxygenated by five freeze-thaw cycles before it was heated up to 70° C. for 48 hours. The reaction was then quenched by liquid nitrogen freezing, and the residue was purified by inducing precipitation by addition of hexane (repeated five times). The structure of the purified product was confirmed by $^1$H NMR to have the foregoing structure:

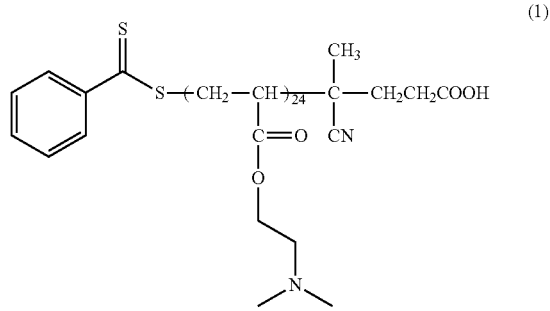

Synthesis of Block Copolymer (2) by Appending a PEG Block onto (1)

PEG(9)-acrylate, methoxy-terminated (3.46 g, 7.2 mmol) was added to a solution containing 30.9 mg (0.009 mmol) of (1) and 0.5 mg (0.0018 mmol) of ACPA in 6 mL of anisole. The mixture was deoxygenated by five freeze-thaw cycles before it was heated up to 65° C. for 8 hours. The reaction was then quenched by liquid nitrogen freezing, and the residue was purified by inducing precipitation by addition of hexane (repeated five times). The structure of the purified product was confirmed by $^1$H NMR and GPC to have the following structure:

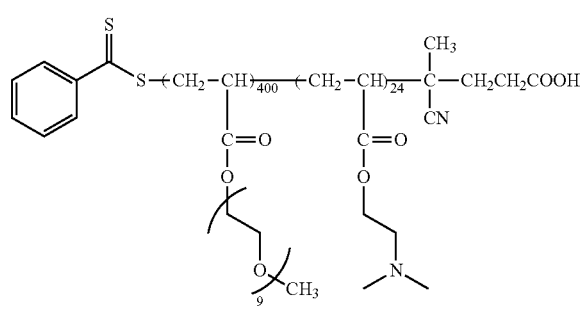

(2)

Synthesis of Quaternary Ammonium Derivative (3) of Block Copolymer (2)

0.3 mL of ethyl bromide was added dropwise into a solution containing 865.9 mg of (2) in 3 mL of acetone at 0° C. The mixture was stirred for 48 hours at room temperature and was then quenched by evaporating the solvent with a nitrogen flow. The residue was dissolved in methylene chloride, and the product was initially purified by inducing precipitation by addition of hexane (repeated five times). The product (3) was then dissolved in 0.01 M PBS (phosphate buffered saline) solution and further purified by dialysis in 0.01 M PBS for 24 hours and deionized water for an additional 48 hours before lyophilization. The structure of the purified product (3) was confirmed by $^1$H NMR and GPC to have the following structure:

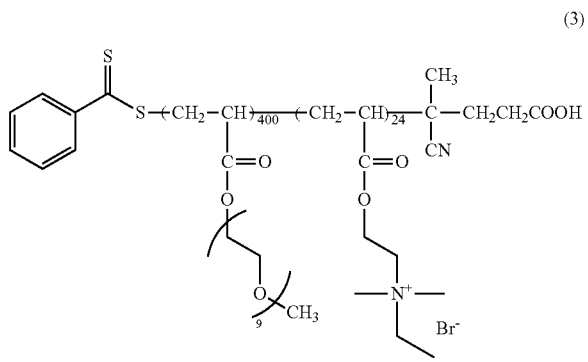

(3)

Evaluation of Lubricating Ability of Block Copolymer (3) on Cartilage

Figure 2:
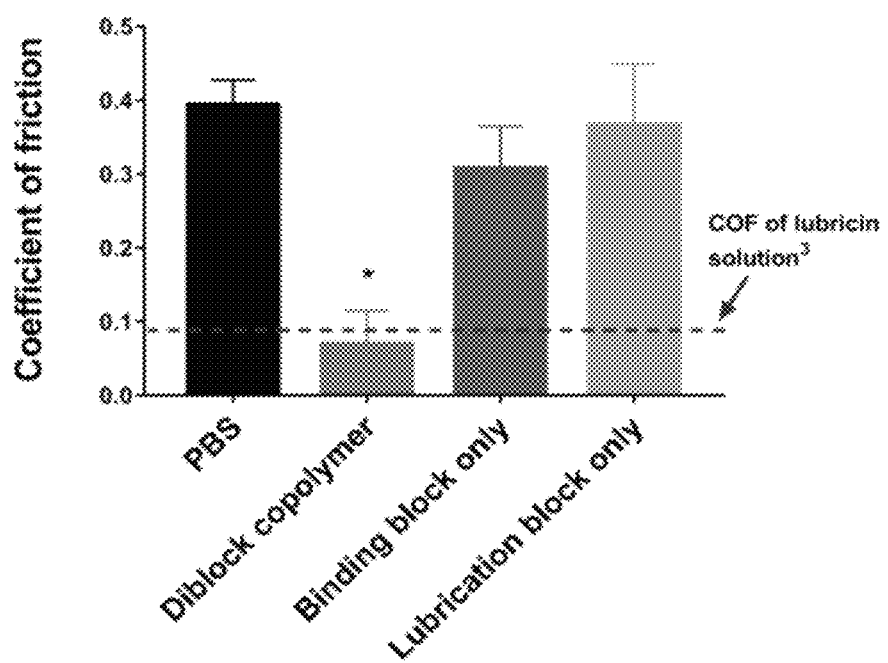
FIG. 2. Graph plotting the coefficient of friction (COF) results for phosphate buffered saline (PBS) solution, the diblock copolymer of FIG. 1, the binding block only, and the lubricating block only.

To evaluate the diblock copolymer (3) as a synthetic lubricant, the tribological behavior of the copolymer was assessed using a custom-built cartilage-on-glass tribometer (Gleghorn, J. P. et al., *J. Orthop. Res.* 2009, 27 (6), 77). Cartilage samples were obtained from the patellofemoral groove of neonatal bovine stifles and incubated in 1.5 M NaCl to remove lubricin. Samples were incubated in PBS and then in polymer solution for 120 minutes to saturate the cartilage surface. After incubation, samples were loaded onto the tribometer in a PBS bath under boundary mode conditions (30% compressive strain and linear oscillation speeds of 0.3 mm/s). To demonstrate the importance of the diblock architecture, individual blocks as binding block only and lubrication block only were also tested under the same condition. FIG. 2 is a graph plotting the coefficient of friction (COF) results for PBS, the diblock copolymer (3), the binding block only, and the lubrication block only. In vitro boundary lubrication testing resulted in a decrease in COF from 0.391±0.020 to 0.088±0.039 (n=4-11, *p<0.0001), which is comparable to the results of lubricin-treated groups (dashed line in FIG. 2, with COF=0.093±0.011)(Gleghorn et al., supra). Notably, a similar trend of decreased COF was not observed with treatment using either of the individual blocks, which suggests that both the binding and lubricating block are needed for boundary lubrication of articular cartilage.

Figure 3:
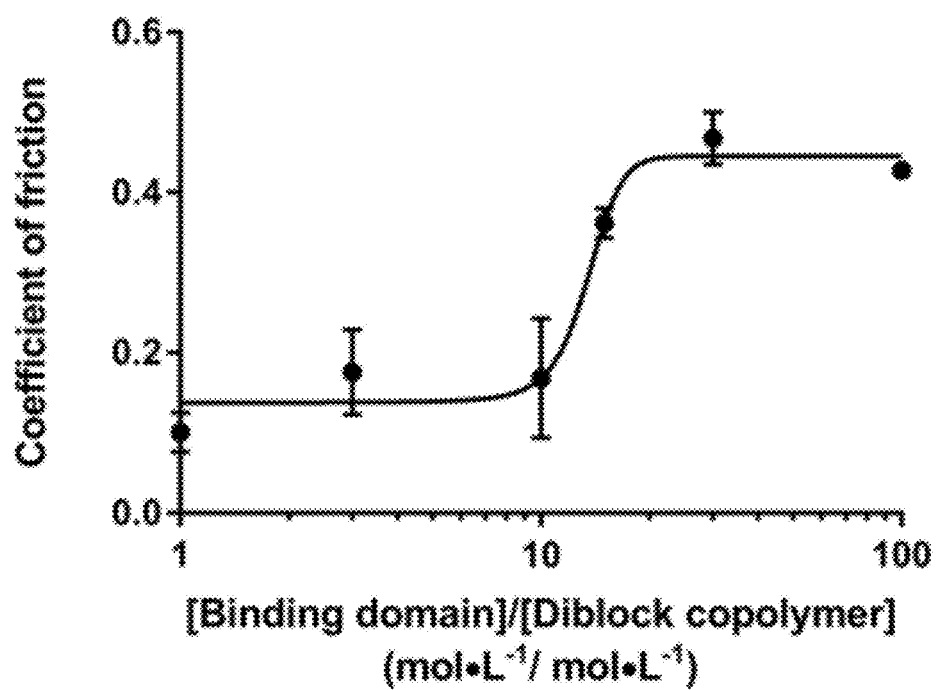
FIG. 3. Graph plotting the COFs of solutions varying in binding block:diblock copolymer ratios, as part of a competitive binding study.

The importance of the binding block for lubrication was further demonstrated by a competitive binding study. COFs of cartilages samples were characterized after exposure to solutions composed of combinations of the binding domain and diblock copolymer in molar ratios of binding block: diblock copolymer ranging from 100:1 to 1:1. FIG. 3 is a graph plotting the COFs of solutions varying in binding block:diblock copolymer (3) ratios. As indicated by the data in FIG. 3, COFs of the samples exhibited dose-response behavior. As expected, high concentrations of the binding domain effectively inhibited lubrication by the diblock copolymer, which suggests that efficiently binding the polymers on the surface is crucial to their success in effectively lubricating cartilage. As shown in FIG. 3, the behavior follows a sigmoidal dose-response ($R^2$=0.87, $IC_{50}$=13.45, n=4-6).

Figure 4:
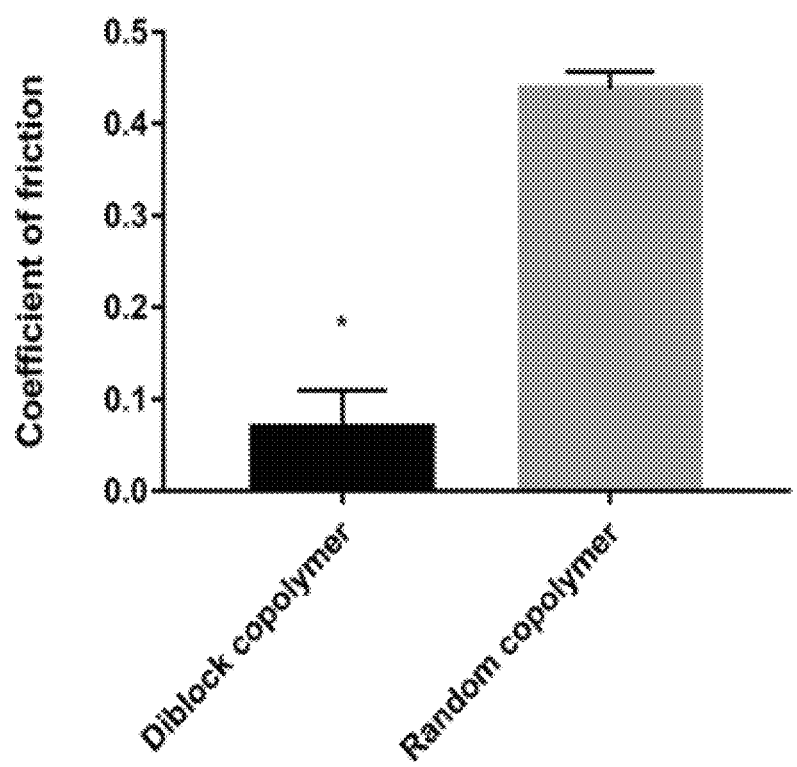
FIG. 4. Graph plotting the COFs of the diblock copolymer of FIG. 1 and a random copolymer version of the diblock copolymer (i.e., same monomeric units but incorporated into the copolymer in random fashion instead of block) as synthesized by random RAFT copolymerization of the two block monomers, followed by quaternary ammonium conversion.

In another experiment, a random copolymer version of the diblock copolymer (i.e., same monomeric units but incorporated into the copolymer in random fashion instead of block) was synthesized by random RAFT copolymerization of the two monomers, followed by quaternary ammonium conversion. FIG. 4 is a graph plotting the COFs (using the same method of tribological testing as described above) of the diblock copolymer (3) and random polymer version. Notably, as indicated by the results in FIG. 4, the random copolymer was significantly less capable in lubricating articular cartilage than the block copolymer. The failure of the random polymer to lubricate the articular cartilage in the same test confirmed the importance of the binding block for providing the significantly improved lubrication ability. In the boundary lubrication mode, frictional properties are primarily governed by solid-solid interactions, and therefore, are largely dependent on the physical and chemical properties of the opposing surfaces. It is critical for the boundary mode lubricant to form a molecular layer that effectively coats the cartilage surface to support the normal load. Individual positively-charged quaternary ammonium groups that are randomly distributed in the polymer backbone are not able to efficiently interact with the cartilage surface, which again, demonstrates the importance of the diblock structure.

Figure 5A:
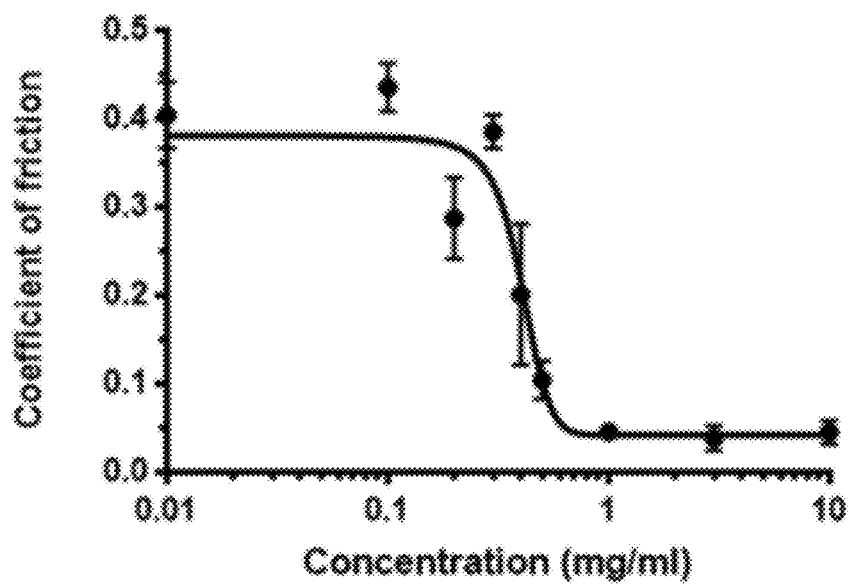
FIGS. 5A, 5B.
Figure 5B:
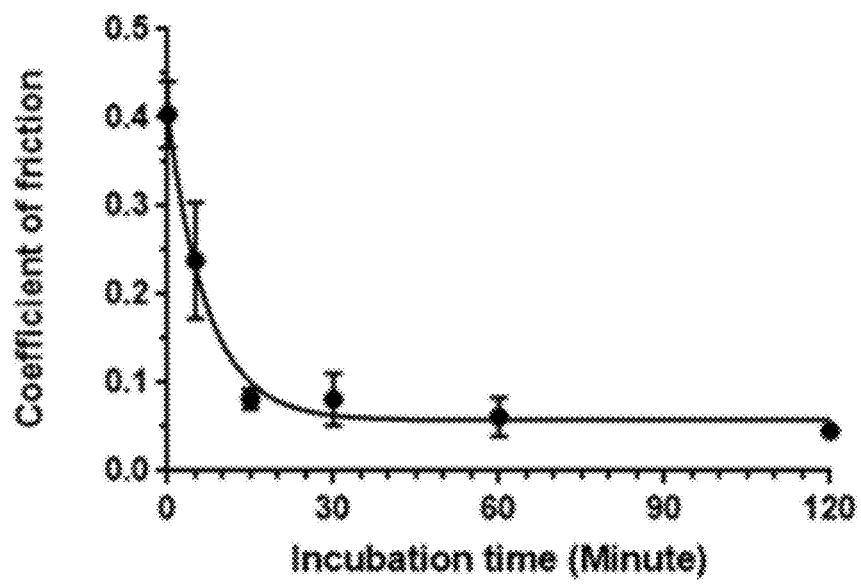

Next, some key lubrication parameters of the diblock copolymer were evaluated and compared to natural lubricin. Briefly, a dosing study was performed using cartilage samples that were treated with solutions of (3) ranging in concentration from 0.01 to 10 mg/mL. FIG. 5A is a graph plotting COF as a function of concentration of the diblock copolymer (3). As indicated by FIG. 5A, the COF of samples exhibited a dose-responsive behavior ($R^2$=0.89) in which high concentrations of copolymer (3) result in effective lubrication of the cartilage ($EC_{50}$=0.404 mg/ml) at a level that is comparable to lubricin ($EC_{50}$ is greater than 0.030 mg/mL under similar conditions). FIG. 5B is a graph plotting COF as a function of incubation time, with 1 mg/mL of diblock copolymer (3) for different durations. The resulting graph can be considered a binding kinetics curve. The concentration was selected using the inflection point of the sigmoidal dosing curve. When fitting into a one-phase decay followed by plateau model ($R^2$=0.95), the binding kinetic curve (FIG. 5B) revealed a binding time constant ($\tau$) of 7.19 minutes, which is comparable to that of natural lubricin (~9 minutes), e.g., Gleghorn et al., supra.

The above results demonstrate the successful design of a diblock copolymer whose architecture mimics the lubricating protein lubricin. Evaluated by a custom tribometer, block copolymer (3) successfully reduced the coefficient of friction of articular cartilage in the boundary mode (0.088±0.039) to a level that is equivalent to natural lubricin (0.093±0.011). Additionally, both the $EC_{50}$ (0.404 mg/mL) and binding time constant (7.19 minutes) of this polymer are comparable to the corresponding parameter of lubricin (>0.03 mg/mL, ~9 minutes). Like lubricin, the outstanding tribological properties of this diblock copolymer can be explained by its molecular architecture. Particularly, efficient binding of this polymer on articular cartilage has been shown to be essential to effective lubrication. The block copolymer (3) has unexpectedly been shown to possess at least the lubrication ability of lubricin, which indicates a significant clinical potential.

Evaluation of Lubricating Ability of Block Copolymer (3) on Bone

In this study, the same block copolymer (3) was tested for its lubricating ability on bone. Bone samples were obtained from the femoral condyle of neonatal bovine stifles. The bone plugs were extracted by a 6 mm diameter drill through the cartilage layer to the growth plate and trimmed to 2 mm in height. The subchondral surface was exposed by removing the cartilage layer, and the trabecular bone plugs were obtained by cutting the medial part of the drilled bone plugs. Bone samples were incubated in PBS solution and then the polymer solution containing (3) (10 mg/mL for 2 hours or 1 mg/mL for 1 hour). The tribological properties were measured on a custom bone-on-glass tribometer (Gleghorn et al., supra) under 450 g normal load and linear oscillation speeds of 0.3, 1, and 3 mm/s. Coefficient of friction was calculated as the average shear force while sliding divided by the normal force. One-way ANOVA and Student's t-test with matched sliding speeds were used to determine the mathematical significance between treatments.

Figure 6A:
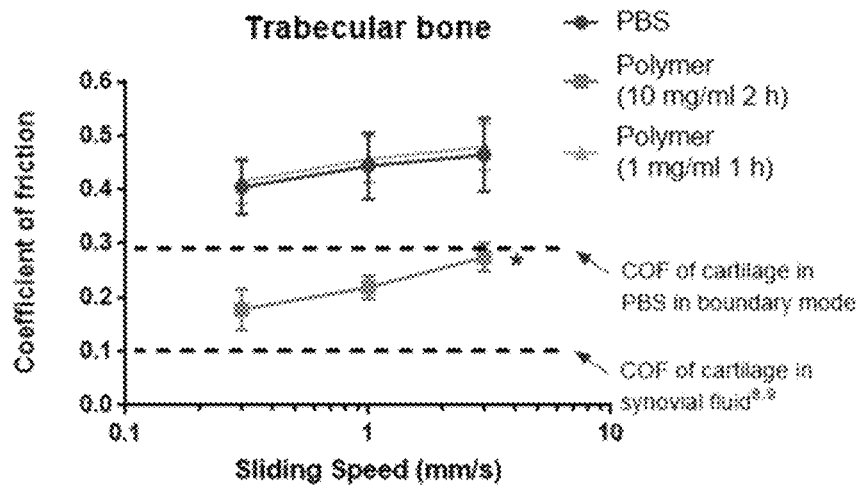
FIGS. 6A, 6B.
Figure 6B:
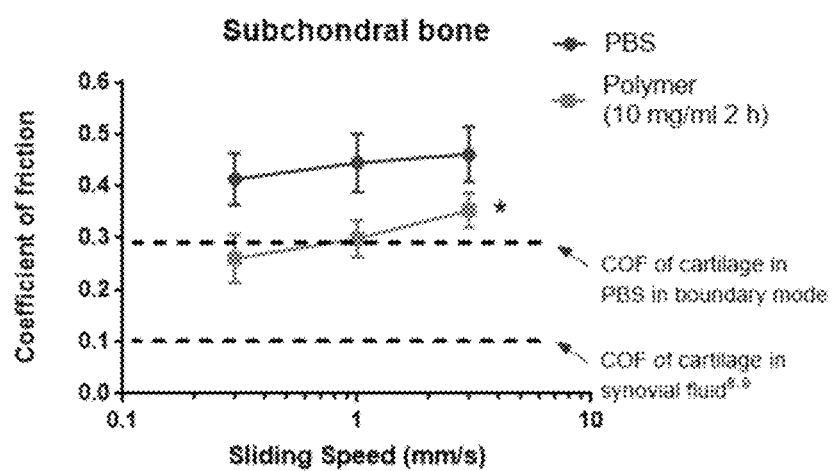

It is well known that the coefficients of friction (COF) of both trabecular and subchondral bones are significantly elevated in comparison to cartilage under the same conditions. FIGS. 6A and 6B are graphs plotting the COF of trabecular and subchondral bone samples, respectively, treated with the diblock copolymer (3) solution (10 mg/mL for 2 hours or 1 mg/mL for 1 hour) or PBS solution. The COF of cartilage in PBS in boundary mode or in synovial fluid is also shown. As shown by the data in FIGS. 6A and 6B, bone plug samples incubated in polymer solution exhibited COFs significantly lower than PBS controls ($\Delta$COF~-0.2 for trabecular bone, p<0.05; $\Delta$COF~-0.15 for subchondral bone, p<0.05). As can also be ascertained by the data in FIGS. 6A and 6B, the lubrication is more improved using a higher concentration (e.g., above 1 mg/mL, or at least 2, 5, or 10 mg/mL) of polymer solution and/or longer incubation time (e.g., more than 1 hour, or at least 1.5 or 2 hours). The results demonstrate that the block copolymers described herein can effectively lubricate cartilage or bone to a level that is comparable or even superior to the COF of cartilage in PBS in the boundary mode. Without being bound by theory, it is believed that the diblock copolymers of the invention strongly interact with negatively charged cartilage or bone mineral components and resist normal compression by virtue of the bottle-brush type of architecture.

While there have been shown and described what are at present considered the preferred embodiments of the invention, those skilled in the art may make various changes and modifications which remain within the scope of the invention defined by the appended claims.

What is claimed is:

1. A block copolymer having the following structure:

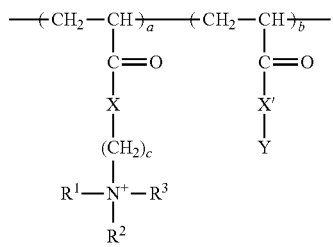

(1)

wherein:
$R^1$, $R^2$, and $R^3$ are independently selected from hydrocarbon groups having at least one and up to twelve carbon atoms;
X and X' are independently selected from —NR'—, —O—, and a bond, wherein R' is selected from hydrogen atom and hydrocarbon groups having at least one and up to six carbon atoms;
Y is a polyalkylene glycol;
subscript a is an integer in a range of 3-40;
subscript b is an integer in a range of 30-500; and
subscript c is an integer of at least 1;
wherein, by the laws of chemistry, the block copolymer is terminated on each end by terminal groups, and the total positive charge of quaternary ammonium groups in the copolymer is counterbalanced by a total negative charge of equivalent magnitude provided by anions associated with said ammonium groups.

2. The block copolymer of claim 1, wherein said polyalkylene glycol is polyethylene glycol.

3. The block copolymer of claim 1, wherein said polyalkylene glycol is constructed of at least two and up to 500 monomer units.

4. The block copolymer of claim 1, wherein said polyalkylene glycol is constructed of at least two and up to 200 monomer units.

5. The block copolymer of claim 1, wherein said polyalkylene glycol is constructed of at least two and up to 100 monomer units.

6. The block copolymer of claim 1, wherein said polyalkylene glycol is constructed of at least two and up to 20 monomer units.

7. The block copolymer of claim 1, wherein $R^1$, $R^2$, and $R^3$ are independently selected from alkyl groups having at least one and up to twelve carbon atoms.

8. The block copolymer of claim 1, wherein at least one of said terminal groups is a thiol group.

9. A method for imparting increased lubricity to a biological tissue, the method comprising contacting said biological tissue with a sufficient amount of a composition to impart increase lubricity, said composition comprising a block copolymer having the following structure:

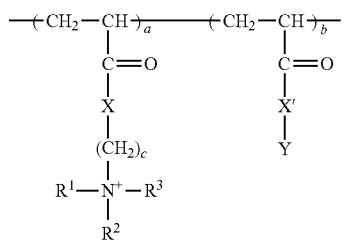

wherein:
$R^1$, $R^2$, and $R^3$ are independently selected from hydrocarbon groups having at least one and up to twelve carbon atoms;
X and X' are independently selected from —NR'—, —O—, and a bond, wherein R' is selected from hydrogen atom and hydrocarbon groups having at least one and up to six carbon atoms;
Y is a polyalkylene glycol;
subscript a is an integer in a range of 3-40;
subscript b is an integer in a range of 30-500; and
subscript c is an integer of at least 1;
wherein, by the laws of chemistry, the block copolymer is terminated on each end by terminal groups, and the total positive charge of quaternary ammonium groups in the copolymer is counterbalanced by a total negative charge of equivalent magnitude provided by anions associated with said ammonium groups.

10. The method of claim 9, wherein at least one of said terminal groups is a thiol group.

11. The method of claim 9, wherein said biological tissue is selected from joints, bone, ocular tissue, nasal tissue, tendons, tendon capsule, and vaginal tissue.

12. A block copolymer having the following structure:

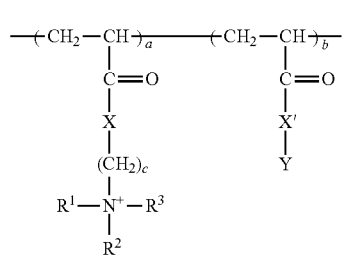

wherein:
$R^1$, $R^2$, and $R^3$ are independently selected from hydrocarbon groups having at least one and up to twelve carbon atoms;
X and X' are independently selected from —NR'—, —O—, and a bond, wherein R' is selected from hydrogen atom and hydrocarbon groups having at least one and up to six carbon atoms;
Y is selected from polyalkylene glycol, saccharide, and polyalcohol;
subscript a is an integer in a range of 3-40;
subscript b is an integer in a range of 30-500; and
subscript c is an integer of at least 1;
wherein, by the laws of chemistry, the block copolymer is terminated on each end by terminal groups, wherein at least one of said terminal groups is a thiol group, and the total positive charge of quaternary ammonium groups in the copolymer is counterbalanced by a total negative charge of equivalent magnitude provided by anions associated with said ammonium groups.

\* \* \* \* \*